United States Patent [19]

Hu

[11] Patent Number: 4,575,041
[45] Date of Patent: Mar. 11, 1986

[54] LIQUID FLOW CONTROLLER

[76] Inventor: Liang-Tung Hu, 3rd Fl., No. 248, Sec: 4, Hsing-Yi Rd., Taipei, Taiwan

[21] Appl. No.: 692,350

[22] Filed: Jan. 17, 1985

[51] Int. Cl.⁴ ............................................. F16L 55/14
[52] U.S. Cl. ........................................: 251/8; 251/4; 604/250
[58] Field of Search ............................ 251/4, 7, 8, 296; 604/250

[56] References Cited

U.S. PATENT DOCUMENTS

| | | | |
|---|---|---|---|
| 2,285,974 | 6/1942 | Huber | 251/8 |
| 3,078,501 | 2/1963 | Thorman | 251/8 |
| 3,410,517 | 11/1968 | Wall | 251/8 |
| 4,176,671 | 12/1979 | Citrin | 251/7 |
| 4,257,446 | 3/1981 | Ray | 251/8 |

Primary Examiner—Martin P. Schwadron
Assistant Examiner—Sheri M. Novack
Attorney, Agent, or Firm—Lowe, King, Price & Becker

[57] ABSTRACT

This invention relates to a controller and in particular to a liquid flow controller for intravenous injection comprising a first cylindrical member provided at one end surface with a pair of threaded tongues which extend outwardly therefrom and form a recess thereof, a flange being properly disposed on said end surface, a second cylindrical member being hollowed and threadedly engaged with said first cylindrical member, an annular member provided at a first end surface with a hole being received within and secured to said second cylindrical member, a controlling rod being inserted into and located within said annular member, a rubber hose partially surrounded by a rubber ring being positioned in said recess and clamped between said flange and said controlling rod, a solid rubber rod being inserted into and received within said rubber hose, and a pair of connectors being disposed on the both terminals of said rubber hose of a better connection.

1 Claim, 12 Drawing Figures

4,575,041

LIQUID FLOW CONTROLLER

BACKGROUND OF THE INVENTION

This invention relates to a controller and in particular to a liquid flow controller for intravenous injection.

It will be readily understood that the intravenous injection is an important medical method for those patients who are in a rather weak physical condition.

Commonly used apparatus for the intravenous injection, as shown in FIG. 9, mainly comprise a liquid bottle, a plug, a long P.V.C. tube, a pair of injectors and a adjustable flow controller. In assembling, a first injector passes through said plug disposed at the outlet of said liquid bottle which is filled with desired liquid and into said liquid bottle, and one end of said P.V.C. tube is connected to said first injector and the other end thereof is connected to a second injector, and a liquid flow controller is properly disposed on said P.V.C. tube and located between said first and second injectors. In operation the liquid will flow from the liquid bottle and through the first injector, the P.V.C. tube, the flow controller, the second injector and into the veins of the patients when one presses said P.V.C. tube. The liquid flow should be controlled by said flow controller according to the physical condition of each patient. However, according to the experience of those patients who have been injected via the veins, the controlling range of said conventional controller is somewhat limited and hence it is not suitable for patients who are extremely weak and need a slower flow rate of intravenous injection. Besides, according to the conventional way, the P.V.C. tube is directly pressed by the flow controller and hence said P.V.C. tube will easily become deformation, therefore it is difficult to obtain a desired flow rate by means of the conventional apparatus.

Accordingly, it is an object of the present invention to obviate the above-mentioned drawbacks.

SUMMARY OF THE INVENTION

It is the primary object of the present invention to provide a liquid flow controller for obtaining a desired liquid flow.

It is another object of the present invention to provide a liquid flow controller, wherein a rubber hose is partially surrounded by a rubber ring for preventing said rubber hose from being directly pressed during adjusting period.

It is still another object of the present invention to provide a liquid flow controller, wherein a solid rubber rod is inserted into and received within said rubber hose for obtaining a desired and accurate liquid flow.

DETAILED DESCRIPTION OF THE PREFERRED EMBODIMENT

Figure 1:
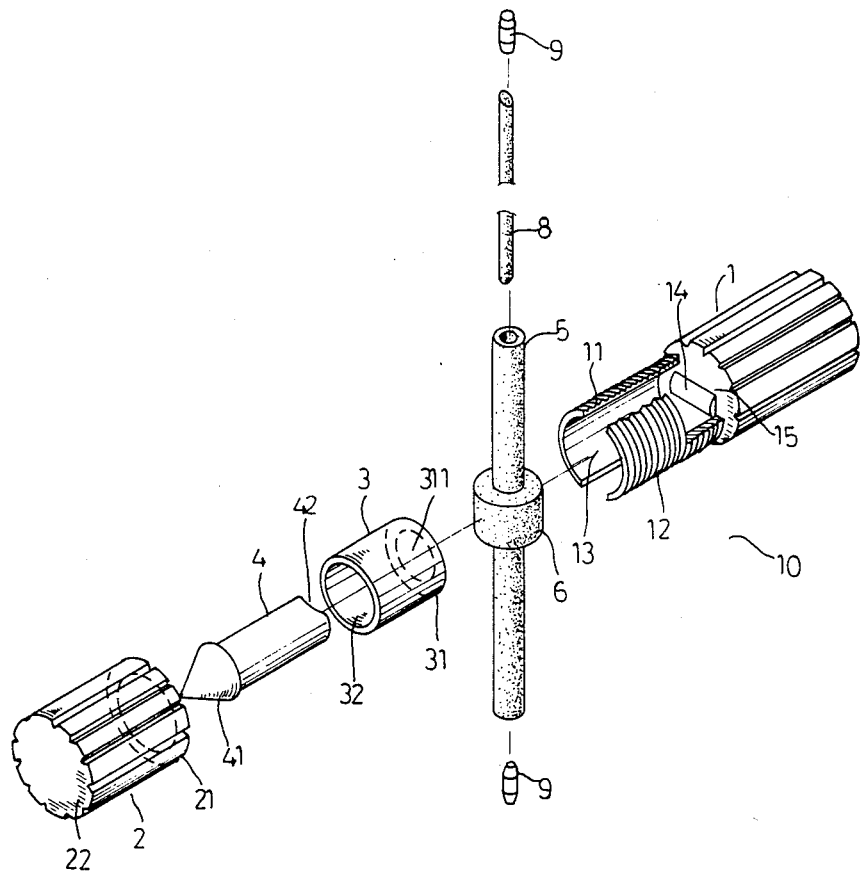
FIG. 1 is a fragemental view of a preferred embodiment of the present invention.
Figure 5:
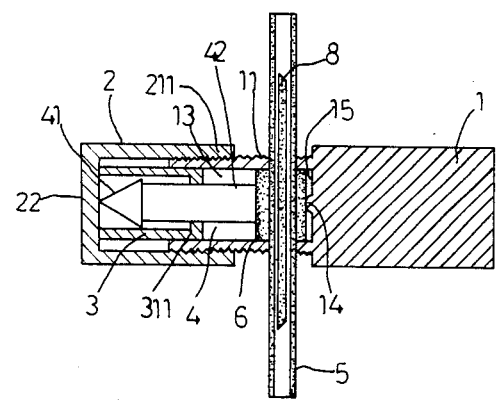
FIG. 5 is a cross-sectional view taken along line 1—1 of FIG. 4.

Referring to the drawings and in particular to FIG. 1, a liquid flow controller (10) according to a preferred embodiment of the present invention comprises a first cylindrical member (1) provided with a pair of threaded tongues (11) (12) which extend outwardly from one end surface (15) of said first cylindrical member (1) and form a recess (13), a flange (14) being properly disposed on said end surface (15), a second cylindrical member (2) being hollowed and provided at a first end (21) with a threaded inner wall (211) (shown in FIG. 5), the other end thereof being provided with a closed second end face (22); an annular member (3) provided at a first end surface (31) with a hole (311), and a second end surface (32) thereof being aperatured, a controlling rod (4) being provided at one terminal with an enlarged end (41) and the other terminal thereof with a concaved end (42), said controlling rod (4) being inserted through said aperatured second end surface (32) and received within said annular member (3) in such a manner that said controlling rod (4) may move back and forth therein and the concaved end (42) thereof, as shown in FIG. 5, may pass said hole (311) and the enlarged end (41) thereof is used to prevent said controlling rod (4) from sliding out of said hole (311) hence to make the controlling rod (4) stay within said annular member (3). Said annular member (3) with said controlling rod (4) received therewithin is inserted through the first end (21) of said second cylindrical member (2) and received therein, and the apertured second end face (32) of said annular member (3) is secured to the second end face (22) of said second cylindrical member (2) to make said annular member (3) rigidly anchored within said second cylindrical member (2). It is noted that the enlarged end (41) of said controlling rod (4) contacts the second end face (22) of said second cylindrical member (2) only at a single point, hence it may reduce the friction between the controlling rod (4) and the second end face (22) to make said controlling rod (4) operated better.

Figure 2:
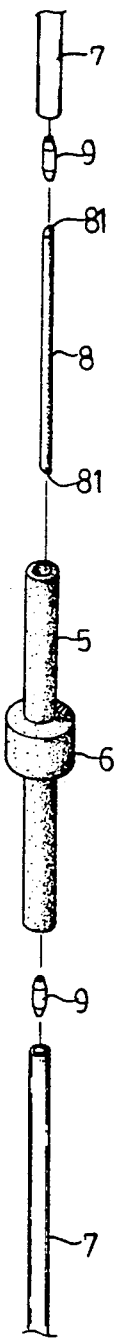
FIG. 2 is a local fragemental view of the present invention.

Referring to FIG. 2, a rubber hose (5) connected between commonly used P.V.C. tubes (7) is partially surrounded by a rubber ring (6) for preventing said rubber hose (5) from being directly pressed by said controlling rod (4), a solid rubber rod (8) is inserted into and received within said rubber hose (5) to form a narrower passage for a accurate liquid flow control, and said rubber ring (6) rubber hose (5) and solid rubber rod (8) are preferably made of medical grade rubber, and a pair of connectors (9) are disposed at the both ends of said rubber hose (5) to provide a better connection. It is noted that the shaved portion (81) of said solid rubber rod (8) is used to prevent the liquid flow in the rubber hose (5) from being stopped in case that said rubber rod (8) contacts with said connectors (9).

Figure 3:
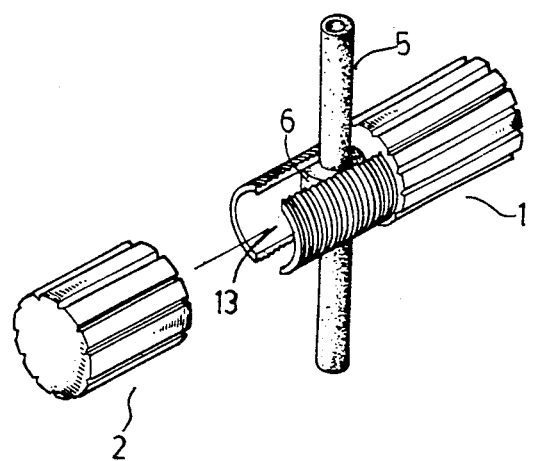
FIG. 3 is a perspective view of a liquid flow controller according to the present invention, where the rubber hose is positioned in a recess formed in the first cylindrical member thereof.

Referring to FIG. 3, the rubber hose (5) together with the rubber ring (6) are properly positioned in the recess (13).

Figure 4:
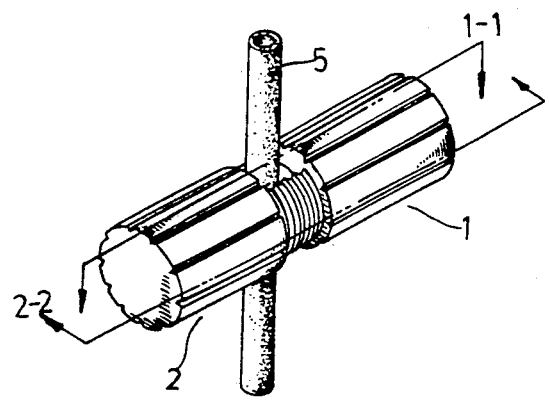
FIG. 4 is a perspective view of a liquid flow controller according to the present invention, where the rubber hose is clamped between the first and second cylindrical members thereof.

In use, referring to FIGS. 4 and 5, the second cylindrical member (2) is adjustably secured to the first cylindrical member (1) by way of the engagement between threaded inner wall (211) and threaded tongues (11) (12), (FIG. 5), and the rubber hose (5) together with the rubber ring (6) are clamped between said controlling rod (4) and the flange (14). When a person properly rotates the second cylindrical member (2) and make said second cylindrical member (2) move towards the first cylindrical member (1), the enlarged end (41) of said controlling rod (4) will be pressed by the second end face (22) of said second cylindrical member (2), and the rubber ring (6) will in turn be pressed by the concaved end (42) of said controlling rod (4) to obtain a desired liquid flow in the rubber hose (5).

Figure 6:
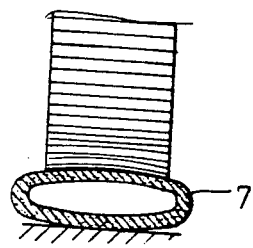
FIG. 6 shows a P.V.C. tube of the prior art which is in a pressed state.
Figure 7A:
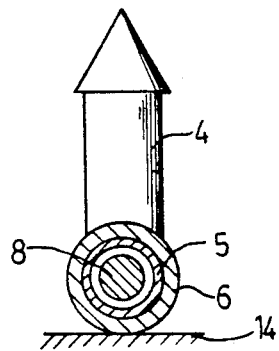
FIG. 7A shows a local cross-sectional view taken along line 2—2 of FIG. 4.
Figure 7B:
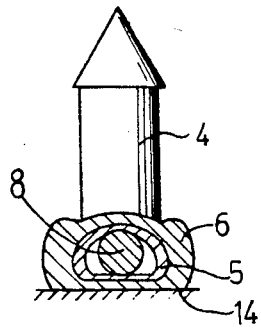
FIG. 7B shows a rubber hose as shown in FIG. 7A, which is in a first pressed state.
Figure 7C:
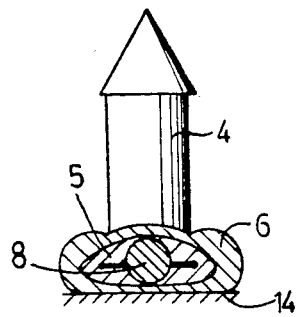
FIG. 7C shows a rubber hose as shown in FIG. 7A which is in a second pressed state.

For illustration, FIG. 6 shows a P.V.C. tube (7) of the prior art which is in a conventional pressed state, and FIG. 7A shows a rubber hose (5) of the present invention which is originally clamped between said controlling rod (4) and said flange (14), and FIG. 7B shows said rubber hose (5) being in a first pressed state which may allow a desired liquid flow to pass therethrough, and FIG. 7C shows said rubber hose (5) being in a second pressed state which may prevent the liquid flow from passing therethrough. Conclusively, it will be apparently understood that the rubber hose (5) of the present invention is able to provide a desired and accurate liquid flow in contrast to the prior art.

Figure 8:
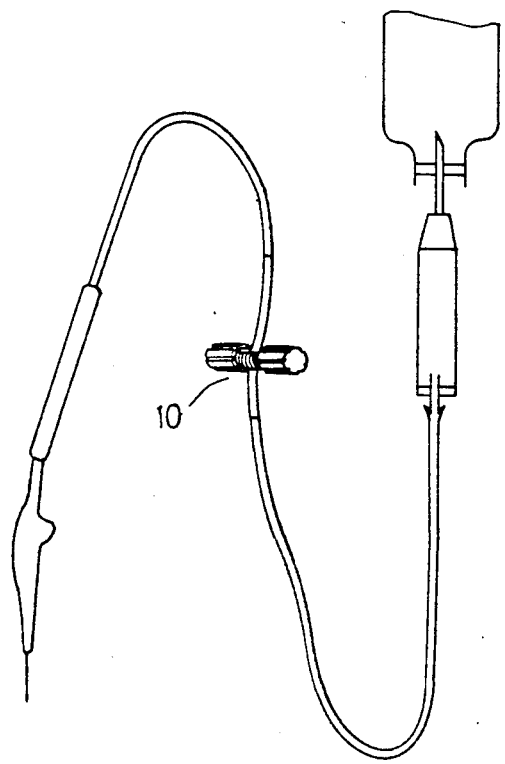
FIG. 8 shows a perspective view of the present invention which is cooperated with the known apparatus which are necessary for intravenous injection.
Figure 9:
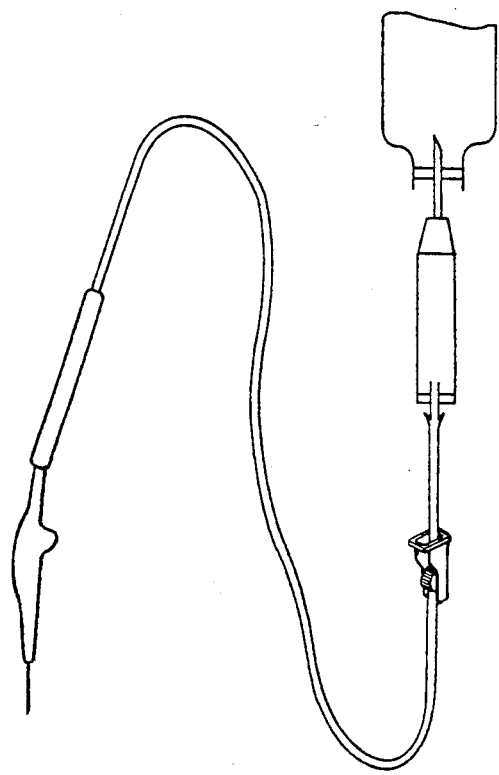
FIG. 9 shows a commonly used apparatus for the intravenous injection.
Figure 10:
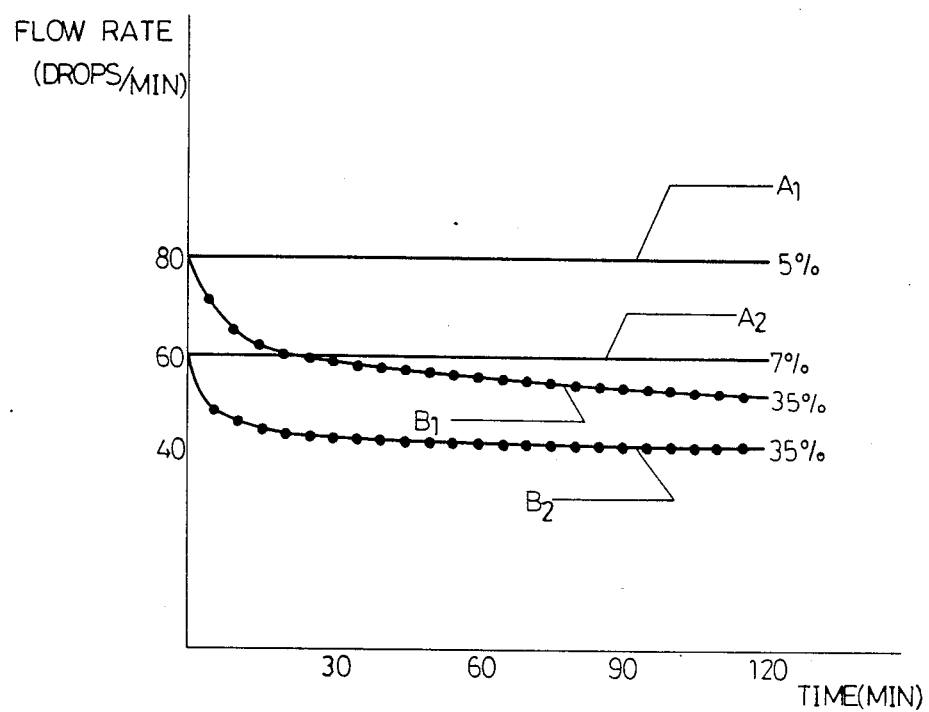
FIG. 10 shows the difference of the liquid flow rates between the present invention and the prior art.

For further illustration FIG. 8 shows a perspective view of the present invention which is cooperated with known apparatus which are necessary for intravenous injection, and FIG. 10 shows the difference of the liquid flow rates between the present invention and the prior art, wherein A1 and A2 respectively represent the present invention with different initial conditions while B1 and B2 respectively represent the prior art of which the initial conditions are similar to those of said present invention. It is seen that the flow rates of A1 and A2, as shown in FIG. 10 are more stable than those of B1 and B2, and hence the present invention is indeed a better liquid flow controller.

I claim:

1. A liquid flow controller comprising:
   a first cylindrical member provided at one end surface with a pair of threaded means which extend outwardly therefrom and form a recess thereof;
   a flange being properly disposed on said end surface;
   a second cylindrical member being hollowed and provided at a first end with a threaded inner wall, the other end thereof being provided with closed second end face, and said second cylindrical member being threadedly engaged with said first cylindrical member;
   an annular member provided at a first end surface with a hole and a second end surface thereof being apertured; said annular member being received within and secured to said second cylindrical member;
   a controlling rod being provided at one terminal with an enlarged end and the other terminal thereof being provided with a concaved end, and said controlling rod being inserted through said apertured second end surface of said annular member and received within said annular member;
   a rubber hose being partially surrounded by a rubber ring for preventing said rubber hose from being directly pressed;
   a solid rubber rod being inserted into and received within said rubber hose;
   a pair of connectors being disposed on the both terminals of said rubber hose; and
   said rubber hose together with said rubber ring being positioned in said recess and clamped between the concaved end of said controlling rod and said flange.

* * * * *